United States Patent [19]

Grooters et al.

[11] Patent Number: 4,779,611

[45] Date of Patent: Oct. 25, 1988

[54] DISPOSABLE SURGICAL SCOPE GUIDE

[76] Inventors: Ronald K. Grooters, 3300 Fuller Rd.; James A. Coil, Jr., 920 - 51st St., both of West Des Moines, Iowa 50265

[21] Appl. No.: 17,712

[22] Filed: Feb. 24, 1987

[51] Int. Cl.$^4$ .............................................. A61M 25/00
[52] U.S. Cl. ......................................... 128/4; 604/96; 604/271
[58] Field of Search ........................ 128/4–8, 128/343–344, 348.1; 604/96–103, 271

[56] References Cited

U.S. PATENT DOCUMENTS

| | | | |
|---|---|---|---|
| 1,089,805 | 3/1914 | Wolf | 604/99 |
| 3,132,645 | 5/1964 | Gasper | 128/3 |
| 3,162,190 | 12/1964 | Del Gizzo | 128/6 |
| 3,417,745 | 12/1968 | Sheldon | 128/6 |
| 3,631,852 | 1/1972 | Hay | 128/3 |
| 3,822,697 | 7/1974 | Komiya | 128/3 |
| 3,860,007 | 1/1975 | Binard et al. | 604/99 |
| 4,180,076 | 12/1979 | Betancourt | 604/101 |
| 4,271,839 | 6/1981 | Fogarty et al. | 604/271 X |
| 4,332,242 | 1/1982 | Chikama | 128/3 |
| 4,341,210 | 7/1982 | Elam | 128/207.15 |
| 4,351,342 | 9/1982 | Wiita | 604/102 |
| 4,392,853 | 7/1983 | Muto | 604/171 |
| 4,470,407 | 9/1984 | Hussein | 128/6 |
| 4,497,318 | 2/1985 | Donmichael | 128/202.28 |
| 4,555,243 | 11/1985 | Markham | 604/263 |
| 4,681,093 | 7/1987 | Ono et al. | 128/6 |

FOREIGN PATENT DOCUMENTS

| | | | |
|---|---|---|---|
| 215350 | 10/1909 | Fed. Rep. of Germany | 604/96 |
| 1511557 | 5/1978 | United Kingdom | 604/271 |

*Primary Examiner*—Dalton L. Truluck
*Attorney, Agent, or Firm*—Zarley, McKee, Thomte, Voorhees & Sease

[57] ABSTRACT

A medical scope guide allows internal body tissues to be viewed. The scope guide includes an elongated hollow tube having opposite inner and outer ends, and a transparent inflatable balloon secured to the inner end of the tube. The outer end of the tube is sealable and is adapted to slidably receive a scope device which extends through the tube and into the balloon. Air can be introduced and released through the tube into and from the balloon for inflating and deflating the balloon. In order to view the internal body tissues, a surgical incision is made in the body of the patient and the scope guide is inserted through the incision such that the inner end of the tube is located within the body and the outer end of the tube is located outside the body. The scope is inserted through the tube and into the balloon and the balloon is inflated so as to engage the body tissues to be observed. The body tissues are viewed with the scope device, which is removed from the scope guide when viewing is completed. The scope guide can remain in position in the body for later viewing of the tissues.

12 Claims, 1 Drawing Sheet

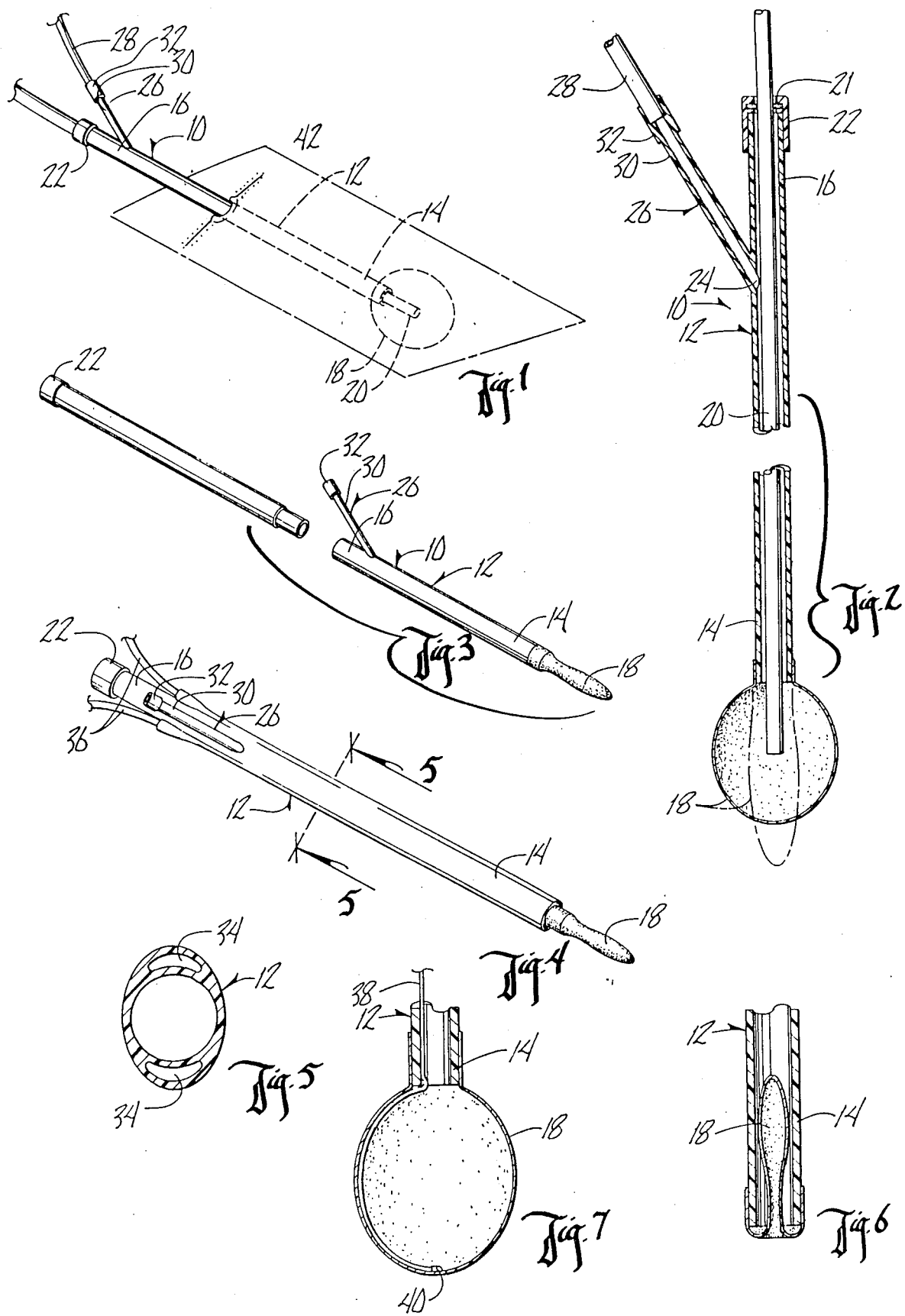

4,779,611

DISPOSABLE SURGICAL SCOPE GUIDE

BACKGROUND OF THE INVENTION

It is often necessary after surgery to be able to see the healing progress of internal body tissues. Also, prior to major surgery, it is desirable to view internal body tissues to determine whether major surgery is necessary. For example, bowel or anastomatic viability can be assessed after bowel surgery where blood supply and viability is questionable. Also, an early assessment of the tissues can be made before necrosis or other complications occur.

Accordingly, a primary objective of the present invention is the provision of a medical scope guide which can be inserted through a surgical incision in the body of a patient for viewing the internal body tissues.

A further objective of the present invention is the provision of a medical scope guide which can be left in the patient's body so that inspection of internal body tissues may take place at a later time.

Another objective of the present invention is the provision of a medical scope guide having an inflatable balloon on the inner end thereof to improve the visibility of the internal body tissues.

Still a further objective of the present invention is the provision of a medical scope guide which includes a vent for aspiration or irrigation of the area surrounding the internal body tissues of concern.

Another objective of the present invention is the provision of a medical scope guide which is disposable.

Still another objective of the present invention is the provision of a medical scope guide which is easy and safe to use and which is economical to manufacture.

A further objective of the present invention is the provision of a method of visually examining the body tissues within the body of a patient by use of a medical scope guide.

These and other objectives will become apparent from the following description of the present invention.

SUMMARY OF THE INVENTION

The present invention is directed towards a medical scope guide for use in viewing the internal body tissues of a patient. The scope guide comprises an elongated hollow tube having opposite inner and outer ends. A transparent balloon is secured to the inner end of the tube. The tube serves as a conduit for air for inflating and deflating the balloon. A scope device is slidably received in the tube and extends into the balloon for viewing internal body tissues.

In use, the scope guide is inserted through a surgical incision into a patient's body. During such insertion, the balloon is retracted into the inner end of the tube. The balloon is inflated, and preferably engages the body tissue to be viewed. After the tube is in place, the scope device is inserted into the tube such that the end of the scope device is positioned within the transparent balloon. Thus, with the balloon inflated and the scope device positioned in the balloon, the internal body tissue can be easily viewed. The scope guide can remain in position with the inner end thereof located within the patient's body and the outer end located outside the patient's body, so that the internal tissues can be viewed at a later time. In such a situation, the incision can be closed around the tube and then closed completely after the scope guide is finally removed.

Preferably, the scope guide is made of a flexible plastic material and is disposable. Also, aspiration and irrigation passages may be provided on the scope guide.

BRIEF DESCRIPTION OF THE DRAWINGS

FIG. 1 is a perspective view showing the medical scope guide of the present invention in position for viewing the internal body tissues of a patient.

FIG. 2 is a sectional view showing the construction of one embodiment of the scope guide with the balloon inflated and the scope device inserted into the scope guide.

FIG. 3 is a perspective view of the scope guide with the balloon deflated and showing an extension member adapted to be connected to the scope guide.

FIG. 4 is a perspective view of a modified embodiment of the scope guide having irrigation and aspiration vents formed therein.

FIG. 5 is a cross-sectional view taken along lines 5—5 of FIG. 4.

FIG. 6 is a partial sectional view showing the balloon retracted into the tube of the scope guide.

FIG. 7 is a partial sectional view showing an optional retraction cord for retracting the balloon into the tube.

DETAILED DESCRIPTION OF THE DRAWINGS

The medical scope guide of the present invention is generally designated in the drawings by the reference numeral 10. Scope guide 10 includes an elongated hollow tube 12 having an inner end 14 and an outer end 16, and a transparent inflatable balloon 18 secured to the inner end of tube 12. Preferably tube 12 is made of a semi-rigid plastic material so as to be flexible. Scope guide 10 is disposable. The outer end 16 of tube 12 is self-sealing and is adapted to slidably receive a scope device 20, as best seen in FIG. 2. Such sealing of outer end 16 is accomplished with a self-sealing membrane 21. In FIG. 2, membrane 21 is shown to be on a sealing cap 22 which fits over outer end 16 of tube 12; however, membrane 21 could be placed directly over outer end 16.

An opening 24 exists in tube 12 adjacent outer end 16 thereof and allows air to be introduced and released through the tube and thus into or from balloon 18, such that the balloon can be inflated or deflated. A conduit 26 may be connected to tube 12 so as to provide an easy connection for an air supply line 28. When supply line 28 is not connected to conduit 26, the outer end 30 of conduit 26 is closed off by a cap 32 so as to prevent the passage of air through tube 12. As an alternative to conduit 26, opening 24 may include a self-sealing membrane similar to membrane 21 through which the air supply line can be inserted for the transmittal of air to and from tube 12 and balloon 18. Also, as an alternative to introducing air into balloon 18 through tube 12, a separate air supply line may be attached in or on tube 12 or may be formed integrally with tube 12.

FIGS. 4 and 5 show an alternative embodiment of tube 12 wherein vent passages 34 are provided. While FIG. 5 shows vent passages 34 to be integrally formed in tube 12, it is understood that separate vent lines can be secured to tube 12 by adhesive or the like. Vent passages 34 allow aspiration and/or irrigation of the body cavity adjacent the internal body tissues to be viewed. Vent passages 34 are connected by lines 36 to a vacuum source when aspiration is desired or to a fluid source when irrigation is desired.

As a safety feature, a retraction cord 38 may optionally be provided. Retraction cord 38 has an inner end 40 attached to the inner wall of balloon 18, as shown in FIG. 7, and extends through tube 12. In the event that balloon 18 fails to deflate when scope guide 10 is to be removed or when otherwise necessary, the outer end (not shown) of retraction cord 38 which extends out of outer end 16 of tube 12 can be pulled such that balloon 18 is retracted into inner end 14 of the tube. A sufficient pulling force will cause a hole to be torn in balloon 18 so as to allow air to escape therefrom.

In operation, scope guide 10 is inserted through an incision 42 in a patient's body such that inner end 14 is located within the body and outer end 16 is located outside the body. Balloon 18 is retracted into inner end 14 of tube 22 as scope guide 10 is inserted through incision 42 into the body cavity, as shown in FIG. 6. When a physician or other medical personnel desires to view the internal body tissues, scope 20 is inserted through tube 12 such that the viewing end of the scope is within balloon 18. Balloon 18 is inflated so that scope device 20 can see the body tissue through the transparent balloon. Preferably, balloon 18 engages the body tissues to be observed when it is inflated, so as to improve the visibility of the tissue.

After the internal body tissues are viewed, scope device 20 is removed from tube 12 and scope guide 10 can be left in position in the patient's body so that the tissue can again be viewed at a later time. Upon removal of scope device 20 from tube 12, outer end 16 of the tube is automatically sealed. Preferably, balloon 18 is deflated after the scope device is removed from the tube.

Incision 42 is closed around tube 12 if the scope guide is to be left in place. When no further viewing of the body tissues is necessary, scope guide 10 can be removed from the patient's body, and incision 42 can be closed completely.

From the foregoing, it is seen that at least all the stated objectives are accomplished by the scope guide of the present invention.

What is claimed is:

1. A post-operative, disposable medical scope guide, comprising:

an elongated flexible, lightweight tube having outer and inner ends and being adapted for partial insertion into a body cavity through a surgical incision to locate said inner end within the body cavity and to locate said outer end outside the body cavity;

said tube having a primary passage extending between said outer and inner ends through which a removable scope means is selectively passed, said primary passage of said tube having a larger diameter than the diameter of said scope means so to provide clearance between said scope means and said tube when said scope means is positioned within said tube;

a transparent inflatable balloon secured to said inner end of said tube;

said primary passage being unobstructed between said inner and outer ends of said tube to define an unobstructed opening into said balloon through which said scope means passes into balloon for viewing internal body tissues;

a sealable airtight means adjacent the outer end of said tube for sealing closed the tube and for maintaining the internal sterility of the tube and being adapted to slidably receive said scope means; and means for selectively introducing and releasing air into and from said balloon for inflation and deflation thereof.

2. The scope guide of claim 1 wherein said means for introducing and releasing air into and from said balloon includes a closable air port on said tube adjacent the outer end thereof for introducing and releasing air through said tube into and from said balloon.

3. The scope guide of claim 1 further comprising at least one vent extending substantially along the length of said tube for aspiration or irrigation of the body cavity.

4. The scope guide of claim 1 further comprising a retraction cord extending through said tube and having an inner end attached to the interior of said balloon and an outer end extending from the outer end of said tube whereby said balloon is retractable into the inner end of said tube by pulling on the outer end of said cord.

5. The scope guide of claim 1 further comprising an elongated hollow guide extension member adapted to be connected to the outer end of said tube for extending the length of said scope guide.

6. The scope guide of claim 1 wherein said means for introducing and releasing air into and from said balloon is in direct communication with said primary passage of said tube such that air is passable through said primary passage when said scope means is positioned within said tube.

7. The scope guide of claim 1 wherein said balloon is initially positioned within said tube and is adapted to be forced out of said tube for inflation outside of said tube.

8. The method of visually examining and monitoring internal post-operative body tissues within the body of a patient, comprising:

making an surgical incision in the body of a patient to gain access to internal body tissues within the patient;

operatively treating said internal body tissues;

inserting through said incision the inner end of a hollow elongated scope guide having a lateral dimension substantially smaller than said surgical incision and having a transparent balloon on said inner end, with said inner end being positioned adjacent said body tissues and with the outer end of said guide being positioned outside said incision;

closing said incision around said guide;

inflating said balloon into engagement with the tissues to be observed;

inserting the viewing end of an elongated scope device into said guide, and moving said viewing end into said balloon member;

viewing said body tissues with said scope device through said transparent balloon after treatment of the tissues so as to monitor the reaction of the tissues to the treatment.

9. The method of claim 7 further comprising, leaving said guide in position with the inner end thereof being within the body and the outer end thereof being outside the body.

10. The method of claim 9 further comprising withdrawing said scope device from said guide when tissues are not being viewed.

11. The method of claim 10 further comprising deflating said balloon when said scope device is not in said guide.

12. The method of claim 7 wherein said balloon is retracted into the inner end of said guide while said guide is being inserted into the body.

* * * * *